(12) United States Patent
Berkland et al.

(10) Patent No.: US 9,814,678 B2
(45) Date of Patent: Nov. 14, 2017

(54) SUSTAINED RELEASE PARTICLE FORMULATIONS

(71) Applicant: ORBIS BIOSCIENCES, INC., Kansas City, KS (US)

(72) Inventors: Cory Berkland, Lawrence, KS (US); Milind Singh, Mission, KS (US)

(73) Assignee: ORBIS BIOSCIENCES, INC., Lenexa, KS (US)

( * ) Notice: Subject to any disclaimer, the term of this patent is extended or adjusted under 35 U.S.C. 154(b) by 0 days.

(21) Appl. No.: 14/302,742

(22) Filed: Jun. 12, 2014

(65) Prior Publication Data

US 2014/0294980 A1 Oct. 2, 2014

Related U.S. Application Data

(63) Continuation of application No. PCT/US2012/069287, filed on Dec. 12, 2012.

(60) Provisional application No. 61/569,655, filed on Dec. 12, 2011.

(51) Int. Cl.
| | | |
|---|---|---|
| *A61K 9/16* | (2006.01) | |
| *A61K 9/14* | (2006.01) | |
| *A61K 31/09* | (2006.01) | |
| *A61K 31/192* | (2006.01) | |

(52) U.S. Cl.
CPC .............. *A61K 9/145* (2013.01); *A61K 9/146* (2013.01); *A61K 9/1611* (2013.01); *A61K 9/1617* (2013.01); *A61K 9/1652* (2013.01); *A61K 31/09* (2013.01); *A61K 31/192* (2013.01)

(58) Field of Classification Search
CPC .................................... A61K 9/14; A61K 9/51
See application file for complete search history.

(56) References Cited

U.S. PATENT DOCUMENTS

| | | | | |
|---|---|---|---|---|
| 4,600,645 | A * | 7/1986 | Ghebre-Sellassie . | A61K 9/5073 424/482 |
| 6,197,349 | B1 * | 3/2001 | Westesen et al. ............. | 424/501 |
| 6,296,842 | B1 * | 10/2001 | Jaworowicz et al. ...... | 424/78.02 |
| 2003/0163103 | A1 * | 8/2003 | Benita ................... | A61K 9/0036 604/367 |
| 2004/0067256 | A1 * | 4/2004 | Juppo .......................... | 424/471 |
| 2004/0142043 | A1 * | 7/2004 | Maeda ................. | A61K 9/0019 424/499 |
| 2004/0157876 | A1 * | 8/2004 | Elema .................. | A61K 9/2009 514/302 |
| 2005/0239845 | A1 * | 10/2005 | Proehl et al. ................. | 514/338 |
| 2006/0099257 | A1 | 5/2006 | Landridge et al. | |
| 2008/0274194 | A1 * | 11/2008 | Miller .................... | A61K 9/146 424/489 |
| 2008/0317843 | A1 * | 12/2008 | Jenkins et al. ................ | 424/456 |

(Continued)

OTHER PUBLICATIONS

M Uner. "Preparation, characterization and physico-chemical properties of Solid Lipid Nanoparticles (SLN) and Nanostructured Lipid Carriers (NLC): Their benefits as colloidal drug carrier systems." Pharmazie, vol. 61(5), 2006, pp. 375-386.*

(Continued)

*Primary Examiner* — Isaac Shomer
(74) *Attorney, Agent, or Firm* — Robert R. Riddle; Matthew S. Gibson; Reed Smith LLP

(57) ABSTRACT

Particles for delivery of active ingredients formed from an active ingredient and a hydrophobic matrix, as well as methods for making such particles.

29 Claims, 12 Drawing Sheets

(56) References Cited

U.S. PATENT DOCUMENTS

2009/0148518 A1* 6/2009 Brown ............... A61K 9/4816
424/457
2009/0197975 A1* 8/2009 Lien et al. ................ 514/783

OTHER PUBLICATIONS

CAS Registry Record for Felodipine (CAS 72509-76-3). Entered STN Nov. 16, 1984. 5 printed pages.*
N. Follonier, E Doelker, ET Cole. "Evaulation of Hot-Melt Extrusion as a New Technique for the Production of Polymer-Based Pellets for Sustained Release Capsules Containing High Loadings of Freely Soluble Drug." Drug Development and Industrial Pharmacy, vol. 20(8), 1994, pp. 1323-1339.*
M Kidokoro, NH Shah, AW Malick, MH Infeld, JW McGinity. "Properties of Tablets Containing Granulations of Ibuprofen and an Acrylic Copolymer Prepared by Thermal Processes." Pharmaceutical Development and Technology, vol. 6(2), 2001, pp. 263-275.*
MM Crowley, A Fredersdorf, B Schroeder, S Kucera, S Prodduturi, MA Repka, JW McGinity. "The influence of guaifenesin and ketoprofen on the properties of hot-melt extruded polyethylene oxide films." European Journal of Pharmaceutical Sciences, vol. 22, 2004, pp. 409-418.*
J Liu, F Zhang, JW McGinity. "Preparation of Lipophilic Matrix Tablets Containing Phenylpropanolamine Hydrochloride Prepared by Hot Melt Extrusion." European Journal of Pharmaceutics and Biopharmaceutics, vol. 52, 2001, pp. 181-190.*
CAS Registry Record for Phenylpropanolamine (CAS# 14838-15-4). Entered STN Nov. 16, 1984, 4 printed pages.*
Netafim. Mesh vs. Micron Conversion Chart. (www.netafimusa.com/data/media/2014/12/Mesh-vs-Micron.pdf, accessed by examiner Sep. 30, 2016, 1 printed page).*
Feb. 26, 2013., Written Opinion of the International Searching Authority for PCT Application No. PCT/US12/69287.
Jun. 17, 2014., International Preliminary Report on Patentability for PCT Application No. PCT/US12/69287.

* cited by examiner

SUSTAINED RELEASE PARTICLE FORMULATIONS

CROSS REFERENCE TO RELATED APPLICATIONS

This application is a continuation of PCT/US12/69287 filed Dec. 12, 2012 which claims priority to U.S. Provisional Application No. 61/569,655, filed Dec. 12, 2011, which is incorporated herein by reference.

BACKGROUND

Modified or sustained release pharmaceutical dosage forms have long been used to optimize drug delivery and enhance patient compliance, especially by reducing the number of doses of medicine the patient must take in a day. The use of sustained release dosage forms has increased due to dosing convenience and potentially reduced adverse effects. Multiple-unit sustained release dosage forms have been used for the delivery of therapeutic agents due to their inherent clinical advantages over single-unit dosage forms. These dosage forms spread out uniformly in the gastrointestinal tract and potentially reduce the risk of local irritation and dose dumping, which are often seen with single-unit dosage forms.

Well known mechanisms by which a dosage form (or drug delivery system) can deliver drug at a modified rate (e.g. sustained or delayed release) include diffusion, erosion, and osmosis. An important objective of modified release dosage forms is to provide a desired blood concentration versus time profile for the drug. Fundamentally, the pharmacokinetic profile for a drug is governed by the rate of absorption of the drug into the blood, and the rate of elimination of the drug from the blood. To be absorbed into the blood (circulatory system), the drug must first be dissolved in the gastrointestinal fluids. For those relatively rapidly absorbed drugs whose dissolution in gastrointestinal fluids is the rate limiting step in drug absorption, controlling the rate of dissolution (i.e. drug release from the dosage form) allows the formulator to control the rate of drug absorption into the circulatory system of a patient.

SUMMARY

The present disclosure relates to particles for delivery of active ingredients and more specifically to particles comprising an active ingredient and a hydrophobic matrix and methods for making such particles.

The features and advantages of the present invention will be readily apparent to those skilled in the art. While numerous changes may be made by those skilled in the art, such changes are within the spirit of the invention.

DRAWINGS

Figure 1:
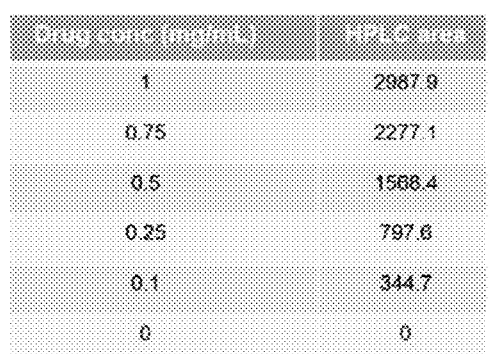
FIG. 1 is a table and graph depicting the relationship between active ingredient concentration and HPLC area.
Figure 1:
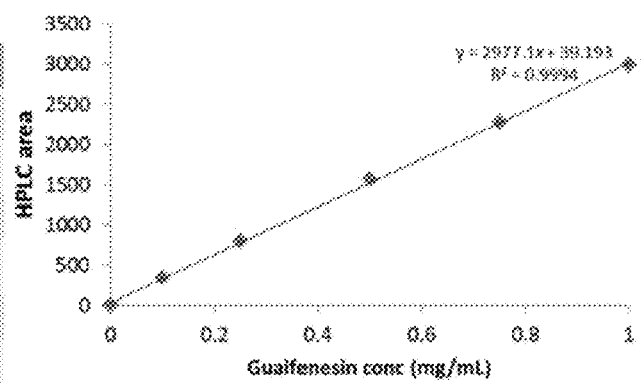

While the present disclosure is susceptible to various modifications and alternative forms, specific example embodiments have been shown in the figures and are described in more detail below. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The present disclosure relates to particles for delivery of active ingredients and more specifically to particles comprising an active ingredient and a hydrophobic matrix and methods for making such particles.

The present disclosure provides, according to certain embodiments, compositions comprising particles, the particles comprising an active ingredient and a hydrophobic matrix. The present disclosure also provides methods for making such particles. The particles of the present disclosure may be useful, among other things, for sustained release formulations for active pharmaceutical ingredients. The particles of the present disclosure also may be useful, among other things, for immediate or fast release formulations of pharmaceutical ingredients.

The active ingredient is disposed within the hydrophobic wax matrix. The active ingredient may be homogenously dispersed within hydrophobic wax matrix via a molten or solubilized form. The active may be dispersed within the hydrophobic matrix in a molecular dispersed form, i.e. as a solid solution, in fine crystalline dispersed form, in a glassy amorphous phase, or dispersed as a fine amorphous powder, as well as in a eutectic mixture. The active ingredient also may be dispersed within hydrophobic wax matrix as small particulates. Alternatively, the active ingredient may be disposed substantially within the hydrophobic wax matrix in a core-shell configuration in which the hydrophobic wax matrix is the shell. As opposed to prior sustained release formulations, the particles of the present disclosure are substantially free of water or other aqueous solvent.

The active ingredient may be any active ingredient so long as it either has a melting point at or below about 250° C. or can be melted together with the hydrophobic matrix to form a co-melt or can be dissolved in one or more components of the hydrophobic matrix. Examples of suitable active ingredients include hydrophilic active ingredients and hydrophobic active ingredients. Other examples of suitable active ingredients include those for which sustained release may be desired. Specific examples of suitable active ingredients having melting temperatures below about 250° C. include, but are not limited to, guaifenesin, metformin hydrochloride, ibuprofen, dextromethorphan HBr, pseudoephedrine HCl, carbinoxamine, clonidine, chlorpheniramine, hydrocodone, azithromycin, methylphenidate HCl, nystatin, ritonavir, and prednisone. Additional suitable hydrophilic active ingredients may be found in Physician's Desk Reference, 66th Edition.

Active ingredients particularly suited for the particles of the present disclosure include those that may be rapidly metabolized. For example, active ingredients with typical plasma half-lives of about one hour, such as guaifenesin. Such short half-lives provide only a short window of therapeutic effectiveness for patients and may benefit from sustained delivery.

In general, the active ingredient may be present in the particles in an amount sufficient to provide any suitable dosage. The active ingredient may be present in the particles in an amount in the range of from about 10% to about 90%, about 15% to about 80%, 20% to about 60%, or 30% to about 40% by weight of the particles.

In certain embodiments, the entire dose of the active ingredient may be provided by the active ingredient in the particle. In other embodiments, the particle provides a partial does of the active ingredient. In such embodiments, the remainder of the does may be included in the composition apart from the particles. For example, the active ingredient may be included in a liquid vehicle in which the particles are suspended.

In general, the particles of the present disclosure have a melting temperature of at least 45° C. and a mean particle size diameter of from about 20 μm to about 500 μm. In certain embodiments, the particles have a mean particle size diameter of from about 50 μm to about 300 μm. In other embodiments, the particles may be substantially monodisperse with a relatively narrow particle size distribution with a 25% or less standard deviation from the mean particle size. In other embodiments, the particles may be substantially monodisperse with a relatively tight particle size distribution within a 5%, 10%, 15%, or 20% standard deviation from the mean particle size. In a specific embodiment, the mean particle diameter may range from 150 μm to 250 μm. In some embodiments, two or more populations of substantially monodisperse particle sizes may be used. The particular particle size, or mixture of particle sizes, will depend on the desired release profile.

In some embodiments, relatively tight particle size distributions may be preferred. Such particle size distributions benefit from the lack of "fines." Particle fines are small particles left over from a manufacturing process. Their small effective surface area results in faster dissolution rates. As used herein, the term "fines" refers to particulates having a particle size at or below 10% of the mean particle size diameter. Accordingly, formulations having particle fines are not substantially monodisperse and may not provide the desired dissolution properties and/or bioavailability.

The hydrophobic matrix may be a hydrophobic wax material, a lipid material, a glycol polymer, or a combination thereof. In certain embodiments, suitable hydrophobic matrix materials have a melting point at or above about 45° C. and a viscosity when melted sufficient to allow spraying.

Suitable lipid materials should be solid at room temperature and have a melting temperature at or above about 45° C. Examples of suitable lipid materials include, but are not limited to, glycerol fatty acid esters, such as triacylglycerols (e.g., tripalmitin, tristearin, glyceryl trilaurate, coconut oil), hydrogenated fats, ceramides, and organic esters from and/or derived from plants, animals, minerals.

Suitable glycol polymers should be solid at room temperature and have a melting temperature at or above about 45° C. Examples of suitable glycol polymers include, but are not limited to, high molecular weight glycols (e.g., polyethylene glycol with a minimum of 20 repeating units), cellulose ethers (e.g., ethyl cellulose, hydroxypropyl cellulose, hydroxypropyl methyl cellulose, microcrystalline cellulose), cellulose esters (e.g., cellulose acetate, cellulose acetate phthalate, hydroxypropyl methyl cellulose phthalate), polyacrylates derivatives, polymethacrylates derivatives, poloxamers, and starch and its derivatives.

In certain embodiments, the hydrophobic matrix may be a hydrophobic wax material. The hydrophobic wax matrix may be any wax-like material suitable for use with the active ingredient. Examples of suitable hydrophobic waxes include, but are not limited to, ceresine wax, beeswax, ozokerite, microcrystalline wax, candelilla wax, montan wax, carnauba wax, paraffin wax, cauassu wax, Japan wax, and Shellac wax.

In certain embodiments of particles employing a hydrophobic wax matrix, the particles further comprise a densifier. A densifier may used to increase the density of a particle. For example, a densifier may be used to make a particle heavier so that it will approach or be closer to the density of a liquid vehicle in which the particles may be suspended. Examples of suitable densifiers include, but are not limited to, titanium dioxide, calcium phosphate, and calcium carbonate. In one embodiment, the one or more densifiers may be present in the particles in an amount in the range of from about 0% to about 40% by weight of the particles.

The hydrophobic matrix may be present in the particles in an amount in the range of from about 5% to about 90%, about 5% to about 30%, about 20% to about 80%, or about 40% to about 60% by weight of the particle. In another embodiment, the hydrophobic matrix may be present in the particles in an amount sufficient to provide sustained release of the active ingredient over a period ranging between about 1 hour to about 12 hours or more. For example, the wax may be present in the particles in an amount sufficient to provide sustained release of the hydrophilic active ingredient over a period of about 1 hour, 2 hours, 4 hours, 6 hours, 8 hours, 10 hours, 12 hours, 18 hours, 24 hours, or longer. In certain embodiments, the hydrophobic matrix may be increased or decreased depending on the particular release characteristics desired. In addition, more than one hydrophobic matrix layer may be used to achieve the particular sustained release desired. In general, higher hydrophobic matrix concentrations favor longer, more sustained release of the active ingredient and lower concentrations favor faster, more immediate release.

In certain embodiments, the particles of the present disclosure comprise a stabilizer. The stabilizer may improve the properties of the hydrophobic wax matrix and provide improved stability of the particles over time, as well as improved dissolution profiles. Changes in particles can occur over time that affect the particle's performance. Such changes include physical, chemical, or dissolution instability. These changes are undesirable as they can affect a formulation's shelf stability, dissolution profile, and bioavailability of the active ingredient. For example the hydrophobic wax matrix or active ingredient may relax into a lower energy state, the particle may become more porous, and the size and interconnectivity of pores may change. Changes in either the active ingredient or hydrophobic wax matrix may affect the performance of the particle. The present disclosure is based, at least in part, on the observation that a stabilizer added to the hydrophobic wax matrix improves the stability and performance of the particles of the present disclosure. By way of explanation, and not of limitation, it is believed that the stabilizer interacts with the hydrophobic wax material making it resistant to physical changes. Accordingly, the particles of the present disclosure comprise a stabilizer. Examples of suitable stabilizers include but are not limited to, cellulose, ethyl cellulose, hydroxyproylmethyl cellulose, microcrystalline cellulose, cellulose acetate, cellulose phthalate, methyl cellylose, chitin, chitosan, pectin, polyacrylates, polymethacrylates, polyvinyl acetate, Elvax® EVA resins, acetate phthalate, polyanhydrides. polyvinylalcohols, silicone elastomers, and mixtures thereof. Stabilizers may be used alone or in combination. The stabilizer may be present in the particles in an amount from about 0.1% to about 10% by weight of the particle. For example, the stabilizer may be present in an amount from about 0.1% to about 5%, about 0.5% to about 2.5%, and about 5% to about 10% by weight of the particle.

In certain embodiments, the particles of the present disclosure also comprise a release modifier. The present disclosure is also based on the observation that a release modifier improves the performance of hydrophobic wax matrix particles particularly during the later stages of the active ingredient's release. The release modifier is believed also to interact with the stabilizer (e.g., improve the stabilizer's solubility) to facilitate preparation of the particles. It is also believed that the release modifier may adjust the relative hydrophobicity of the hydrophobic wax material. Examples of suitable release modifiers include but are not limited to, stearic acid, sodium stearate, magnesium stearate, glyceryl monostearate, cremophor (castor oil), oleic acid, sodium oleate, lauric acid, sodium laurate, myristic acid, sodium myristate, vegetable oils, coconut oil, mono-, di-, tri-glycerides, stearyl alcohol, span 20, span 80, and polyethylene glycol (PEG). Release modifiers may be used alone or in combination. For example, in certain embodiments, the release modifier may be a combination of stearic acid and glyceryl mono stearate. The release modifier may be present in the particles in an amount from about 0.5% to about 90% by weight of the particle. For example, the release modifier may be present in an amount from about 0.5% to about 10%, about 1% to about 5%, about 2.5% to about 5%, about 5% to about 10%, about 10% to about 25%, about 20% to about 90%, about 40% to about 80%, about 50% to about 70%, about 60% to about 80%, and about 80% to about 90% by weight of the particle. In general, higher release modifier concentrations favor faster release of the active ingredient and lower concentrations favor longer, sustained release.

In some embodiments, the particles of the present disclosure may further comprise pharmaceutically acceptable inactive ingredients. The term "pharmaceutically acceptable," when used in connection with the pharmaceutical compositions of the disclosure, refers to molecular entities and compositions that are physiologically tolerable and do not typically produce untoward reactions when administered to a human. For example, "pharmaceutically acceptable" may refer to inactive ingredients approved by a regulatory agency of the Federal or a state government or listed in the U.S. Pharmacopeia or other generally recognized pharmacopeia for use in animals, and more particularly in humans. Examples of inactive ingredients that may be included in particles or formulations of the present disclosure include but are not limited to, buffers, preservative, suspending agents, dyes, antioxidants, surfactants, and the like.

In some embodiments, the particles of the present disclosure may comprise an additional layer disposed on the surface of the particle. Such layers may be used to reduce or delay the release of active ingredient from the particles or to mask the taste of the active ingredient. The additional layer may be a coating applied to the surface of the particle. Such coating may be formed from any material capable of being applied to a pharmaceutical composition. Coatings may be applied to the particles using techniques known in the art such as, for example, Wurster coating and techniques described in U.S. Pat. Nos. 6,669,961, 7,309,500, and 7,368,130, all of which are incorporated by reference.

Examples of suitable materials that may be applied to the surface of the particle to, among other things, reduce or delay the release of active ingredient from the particles include, but are not limited to, polymethacrylates, materials from Eudragit®, Surelease® or Kollicoat® series, and cellulose materials (e.g., ethyl cellulose, hydroxypropylmethyl cellulose).

Examples of suitable materials that may be applied to the surface of the particle to, among other things, mask the taste of the active ingredient include, but are not limited to, mono-, di-, or polysaccharides, sugar alcohols, or other polyols such as lactose, glucose, raffinose, melezitose, lactitol, mannitol, maltitol, trehalose, sucrose, and starch; ethyl cellulose, methyl cellulose, hydroxypropyl cellulose, hydroxypropyl methylcellulose, hydroxybutyl methylcellulose, cellulose propionate, cellulose acetate propionate, cellulose acetate butyrate, cellulose acetate phthalate, carboxymethyl cellulose, cellulose triacetate, polymethyl methacrylate, polyethyl methacrylate, polyphenyl methacrylate, polymethyl acrylate, polyisopropyl acrylate, polyisobutyl acrylate, polyisobutyl methacrylate, polyhexyl methacrylate, polyphenyl methacrylate, polyvinyl acetate, polyvinyl isobutyl ether, polyvinyl alcohol, polyethylene terephthalate, polyethylene oxide, polyethylene glycol, polyethylene, polypropylene, polyoctadecyl acrylate, polyvinyl chloride, and polyvinyl pyrrolidone.

In one embodiment, the additional layer may comprise the hydrophobic matrix and optionally an active ingredient. The additional layer also may further comprise a stabilizer or a release modifier or both. When included, the active ingredient may be present the same or different amounts than is present in the remainder of the particle. Such additional layer may further include a coating as described above.

In certain embodiments, the particles of the present disclosure are stable. Stability is an important consideration for pharmaceutical formulations. For solid dosage forms, like the particles of the present disclosure, stability may be measured with reference to dissolution. Dissolution testing is an in vitro method that characterizes how an API is extracted out of a solid dosage form. It can indicate the efficiency of in vivo dissolution. Dissolution can be measured using standard protocols. As used herein, the term stable or stability refers to particles of the present disclosure that show a standard deviation of 10% or less in the release profile at any given time point during the course of dissolution when placed at 40° C. for up to at least 4 weeks as measured by United States Pharmacopeia (USP) II dissolution.

The present disclosure also provides formulations comprising particles of the present disclosure. Such formulations may be in the form of a suspension of particles, tablets, capsules, or any other suitable means of formulating particulates into dosage forms suitable for administration to a patient. In certain embodiments, formulations of the present disclosure may further comprise a liquid vehicle. As mentioned above, the liquid vehicle may comprise guaifenesin, which may be in dissolved or suspended form. The liquid vehicle may be aqueous based and may include any component suitable for use in a liquid vehicle as is well known in the art. For example, the liquid vehicle may include one or more of a filler, a sugar, a salt, a viscosity modifier, colorants, preservatives, and the like. Additionally, the liquid vehicle may comprise an active ingredient. The active ingredient in the liquid vehicle may be the same or different from the active ingredient in the particles.

In general, the particles of the present disclosure may be made using methods comprising melting the particle components together followed by particle fabrication. Such procedures may be performed in essentially a single step and without the use of water or other aqueous solvent. This has several advantages. For example, the resulting particles are dry and ready for further processing or formulation. Similarly, the resulting particles are substantially free of water, which may improve the stability of the active ingredient. The lack of water in the particles prevents the occurrence of pores or voids in the particle resulting from evaporation of water droplets within the particle. Because the particles can be made without water or an emulsion step, the particles can be formed more efficiently and with fewer manufacturing artifacts. These procedures also allow higher concentrations of active ingredient to be loaded in the hydrophobic wax matrix. Similar, the procedures of the present disclosure offer encapsulation efficiencies for the active reaching greater than 90%. Additionally, the procedure provides particles substantially free of fines, the presence of which can adversely affect the active ingredient's release profile.

In certain embodiments, the particles of the present disclosure may be made by melting the components together using a melt-assisted dissolution of the active ingredient approach followed by particle fabrication. For example, particles of the present disclosure may be made by adding to a preheated vessel the following components: a hydrophobic matrix and an active ingredient, and optionally a releasing agent. The active may be added in a solid form (for melt processing), or in a solubilized form (for creating a solid dispersion). The components are then melted and allowed to equilibrate at a temperature of close to or higher than the melting temperature of the hydrophobic matrix. The stabilizer may be added and allowed to dissolve into the mixture. The temperature of the resulting mixture is then allowed cool to a lower temperature at which the melted solution or suspension still remains processable for particle fabrication. The particle fabrication may use the techniques disclosed in techniques described in U.S. Pat. Nos. 6,669,961; 7,309,500; and 7,368,130, all of which are incorporated by reference. Particle fabrication also may use other techniques known in the art such as, for example, a spinning disk atomizer, centrifugal coextrusion, prilling, spray congealing, spray cooling, melt atomization, and melt congealing.

In certain embodiments, the particles of the present disclosure may be made by melting the components together using a solvent-assisted dissolution of the active ingredient approach followed by particle fabrication. Such approaches are particularly suited for active ingredients with very high melting temperatures. For example, particles of the present disclosure may be made by adding to a preheated vessel the following components: a hydrophobic matrix and a releasing agent. The components are then melted and allowed to equilibrate at a temperature close to or higher than the melting temperature of the hydrophobic matrix. The stabilizer may be added and allowed to dissolve into the mixture. Finally, the drug is solubilized separately in a mild nonflammable solvent and added to the vessel. The solvent is then evaporated from the vessel under constant stirring over a desired duration. The temperature of the resulting mixture is then allowed cool to a lower temperature at which the melted solution or suspension still remains processable for particle fabrication. The particle fabrication is then performed using the techniques herein.

In another embodiment, the particles of the present disclosure may be using a similar melt-assisted dissolution of the active ingredient approach in which the releasing agent and stabilizer are introduced into a preheated vessel and allowed to solubilize at a temperature close to or higher than the melting temperature of the hydrophobic matrix (e.g., for about 5-20 minutes). In operation, the releasing agent in its molten form may be used to substantially solubilize the stabilizer. If needed, this mixture's temperature is then reduced to lower values close to or higher than the melting temperature of the hydrophobic matrix and the hydrophobic wax and active ingredient (e.g., guaifenesin) are then added. The resulting combination is mixed well (e.g., 1 hour) while the temperature is maintained. After mixing, the temperature of the mixture is allowed cool to a lower temperature at which the melted solution or suspension still remains processable before starting the particle fabrication using techniques described above.

In certain embodiments, after particle fabrication the particles may be treated to reduce the occurrence of pores on the surface of the particle. In this approach, the particles are allowed to cool to room temperature (e.g., over about 6 to 24 hours) then exposed to a brief heat treatment at, for example, 65° C. or other temperature slightly lower than the melting temperature of the hydrophobic matrix or other component of the particle having the lowest melting temperature. Such heat treatment may reduce the occurrence of a burst of active ingredient in the release profile of the particle.

One embodiment of the present disclosure is a system for forming particles. The system comprises a coaxial multi-nozzle systems connected to appropriate instruments for the control of flow rates of the feed materials, injection charge, vibration induced to the nozzle and temperature, and for visual characterization of the resulting particles, all of which can either be controlled by a computer or in a stand-alone manner This apparatus can be controlled by a computer which utilizes user-defined optimized processing conditions for fabricating certain spheres of particular interest and would allow the instruments to produce the desired spheres.

Figure 3:
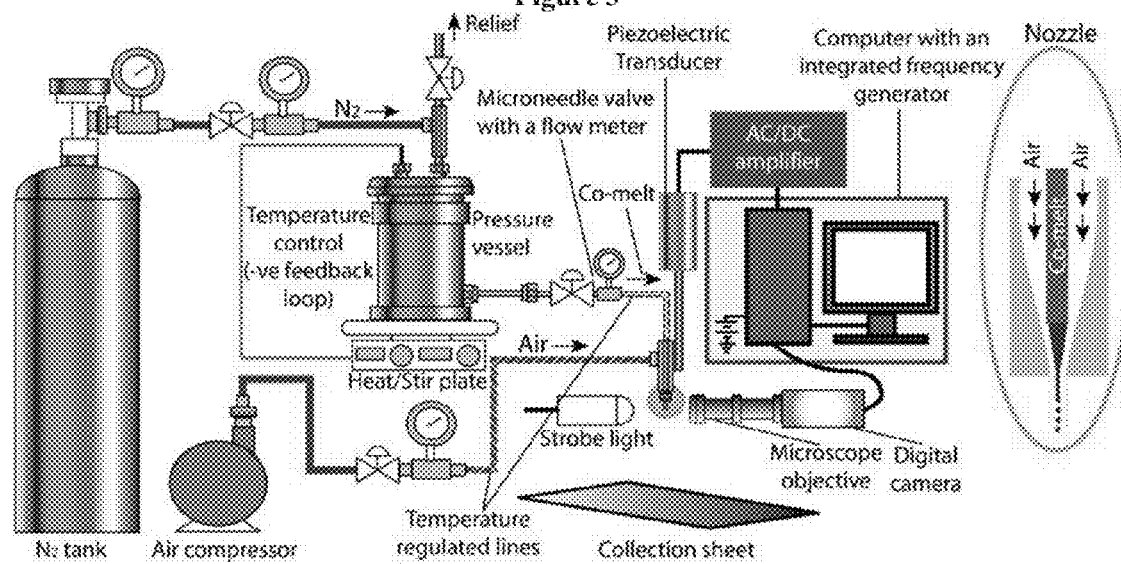
FIG. 3 is a diagram showing a procedure and system used to form particles of the present disclosure, according to one embodiment.

A schematic showing one example of a procedure for making particles of the present disclosure and a system for forming particles of the present disclosure is shown in FIG. 3. Briefly, the apparatus contains a pressurized vessel to which a multi-nozzle is connected. The feed material is passed through the nozzle, which forms a thick laminar jet as it comes out from the nozzle. A carrier stream of air is used to bring the jet diameter down to the desired levels without inducing any turbulence. This thinned jet of feed material is then disrupted into uniform droplets via an acoustic wave excitation generated by an piezoelectric transducer driven by an amplified sinusoidal signal and tuned to the required frequency. The system is monitored using a camera.

To further illustrate various illustrative embodiments of the present disclosure, the following examples are provided.

EXAMPLES

The examples herein are illustrations of various embodiments of this invention and are not intended to limit it in any way.

Example 1

Particles Containing Guaifenesin

An exemplary formulation was developed to match the Mucinex™ Max 1200 mg dose. The particles for this formulation were formed with 45.5% (by weight) candelilla, 32% guaifenesin, 2.5% filler, 10% $TiO_2$ densifier, 10% $CaCO_3$ densifier, which corresponds to an amount per dose/day (based on Mucinex™ Max dose) of 1351 mg, 1200 mg (950 mg in the particles and 250 mg in the vehicle), 74 mg, 297 mg, 297 mg, respectively. The vehicle included 90 g/100 mL high fructose corn syrup, 36 g/100 mL Neosorb 70/02 (Neosorb 70% sorbitol solution), 10 g/100 mL glycerin, 5% wt/wt SCD (sodium citrate dehydrate), 3% wt/wt NaCl, 2.5% wt/wt MMSP (monobasic monohydrate sodium phosphate) 1% wt/wt sodium acetate.

Equilibrium Solubility Determination Protocol. The objective of this example was to determine the drug loading in the particles using "HPLC protocol". About 500 mg of guaifenesin was added into 20 ml of a liquid vehicle. The suspend solution were then shaken and then placed at 40° for two days. The supernatant was then filtered off using a syringe with a 0.45 μm filter, and diluted so that the absorbencies fell within the UV (25-fold dilution). The diluted clear solutions were equilibrium solubility samples, termed as "samples" in the "HPLC protocol'. The "HPLC protocol" was then followed (See below).

Loading Determination Protocol. The objective of this example was to determine the drug loading in the particles using "HPLC protocol." About 40 mg of particles (assuming about a 32% theoretic drug loading) were added to 20 mL of DI water in a scintillation vial. The vial was heated to around 90-110° C. using a heat/stir plate. One the wax melted, the vials were cooled down and the liquid was filtered using a syringe with a 0.45 μm filter. The collected clear solutions were loading samples, termed as "samples" in the "HPLC protocol." The "HPLC protocol" was then followed (See below).

USP II Dissolution Protocol. The objective of this example was to determine the dissolution profile of particles over a period of 12 h, and compare the dissolution profile to Mucinex™ Max.

A liquid vehicle (20 mL) was transferred to glass scintillation vials and 250 mg of pure guaifenesin was added to each vial. This drug suspension was vortexed for 2-3 min at 500 rpm and was then left in an environmental chamber at 40° C. for 48 h to saturate the liquid with the immediate release (IR) guaifenesin.

The dissolution study was performed using a Vanderkamp 600 six-spindle dissolution tester with Hanson 900 mL dissolution jars. The temperature of the medium was maintained at (37±1)° C. The distance between the impeller and dissolution jar bottom was fixed at 2.5 cm, and the impeller rotation speed was fixed at 75 rpm. Mucinex™ Max was used as a positive reference control group. Drug loading in Orbis microspheres was determined (see Example 2), which was found to be 32%.

The amount of particles used for each group was selected to keep the drug load constant, and was matched to the drug load of the control group (i.e., 1200 mg). Since 250 mg guaifenesin is present in the liquid vehicle in the IR form, the sustained release (SR) contribution from the particles was fixed at 950 mg. This equates to 2.97 g of particles per vessel (with 32% drug loading in the particles). Immediately before the dissolution testing, 2.9 g of particles were mixed with the liquid IR formulation (which contained 250 mg of guaifenesin in the IR form) in the same scintillation vials. The particle-liquid formulation was transferred to the dissolution vessel. 880 ml of 0.1 N HCl with 0.05% (v/v) of Tween 80 was added to each vessel (Note: the dissolution solution was pre-equilibrated at 37° C. Also, 50 mL of 880 mL dissolution solution was used to wash each scintillation vial to ensure complete recovery of the particles from the scintillation vial). The temperature of the medium was maintained at 37±1° C. For each sampling, 1.0 ml of dissolution media was sampled at 1, 2, 6, and 12 h, which were then analyzed using HPLC.

HPLC Protocol. The objective of this example was to analyze the samples using HPLC and determine the drug loading using a standard curve for the drug.

A 20 mL of stock solution of the drug was prepared in DI water at a concentration of 1 mg/mL. The solution was left at room temperature for 5 min to get the drug dissolved. The stock solution was appropriately diluted to get several concentrations ranging from 0.1 mg/mL to 1 mg/mL (See FIG. 1). Samples were prepared by appropriately diluting the samples collected using "USP dissolution protocol" to ensure that the drug concentration level falls within the range of the standard curve (e.g., 2× dilution).

HPLC was prepared by first washing the column with the wash buffer (acetonitrile:water 50:50 (v/v)) for 10 min. The HPLC was then primed with the mobile phase based on the following conditions: injection volume=25 μm, flow rate=1.0 ml/minutes, detector UV at 254 nm, mobile phase (620:390) 0.023 M sodium dodecyl sulfate and 0.02 M ammonium nitrate:acetonitrile, and retention time=2.2 minutes. The standards/samples were then run. After the run was over, the column was washed with the wash buffer. The mobile phase was stored in refrigerated condition until used. During the HPLC area determination analysis, to ensure that the baseline was correctly placed, the "Baseline now" was set to 2 min, which ensured a correct baseline for the retention period of 2.2-2.3 min.

Figure 2:
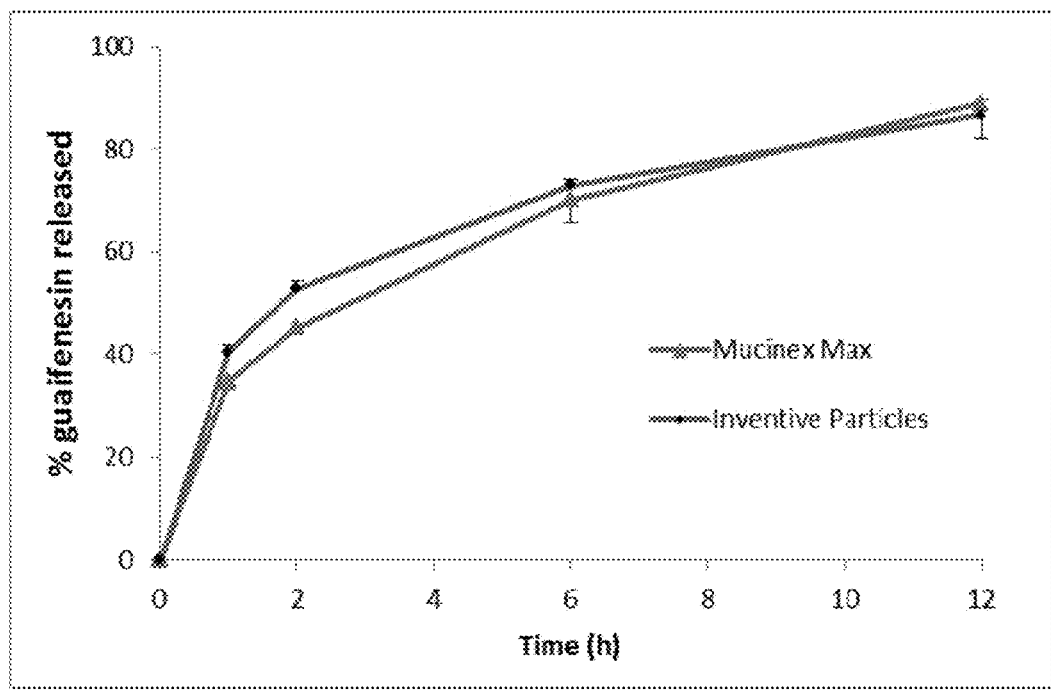
FIG. 2 is a graph depicting the relationship between time and the release of guaifenesin.

The results of this example showed an equilibrium solubility of the liquid vehicle 9.59±0.34 mg/mL (n=3). The drug loading in the particles was found to be about 32%. The USP II dissolution test results (See FIG. 2) were as follows:

| Time (h) | Target % release | Mucinex ™ Max* | Inventive formulation** |
|---|---|---|---|
| 1 | <45% | 34.8 ± 1.1% | 40.4 ± 1.3% |
| 2 | 40%-55% | 45.1 ± 1.0% | 52.7 ± 1.5% |
| 6 | 62%-80% | 70.0 ± 4.3% | 72.9 ± 1.3% |
| 12 | >85% | 88.9 ± 6.8% | 86.6 ± 3.0% |

*Mean ± standard deviation (n = 6)
**Mean ± standard deviation (n = 3)

Example 2

Particles Containing Guaifenesin

Figure 8:
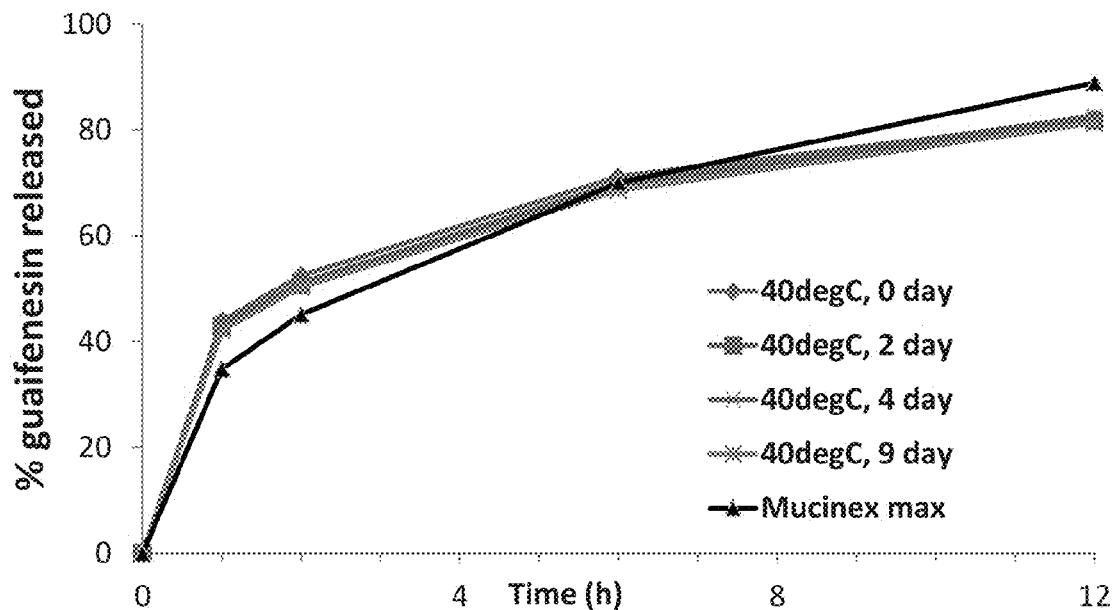
FIG. 8 is a graph showing the relationship between time and the release of guaifenesin.

An exemplary guaifenesin particle was formed with 65% carnauba wax, 2% stearic acid, 32% guaifenesin, and 1% ethyl cellulose. The release of guaifenesin from these particles was measured at 40° C. over 21 days as follows. Samples were kept at 40° C. in an environmental chamber in closed glass vials for the duration of the study. At each day indicated in Table 2, samples were taken out from the incubator, allowed to cool down to room temperature and the release of guaifenesin from the particles over 12 hours was determined according to the USP II dissolution study described above. The results are shown in FIG. 8 and Table 2.

TABLE 2

| | Percent Release | | | |
|---|---|---|---|---|
| Time (h) | Day 0 | Day 2 | Day 4 | Day 9 |
| 0 | 0.0 | 0.0 | 0.0 | 0.0 |
| 1 | 44.0 | 42.7 | 43.0 | 42.1 |
| 2 | 52.5 | 50.7 | 51.2 | 50.3 |
| 6 | 71.2 | 69.6 | 70.0 | 68.5 |
| 12 | 82.2 | 81.7 | 82.7 | 81.3 |

Example 3

Particles Containing Guaifenesin

Figure 9:
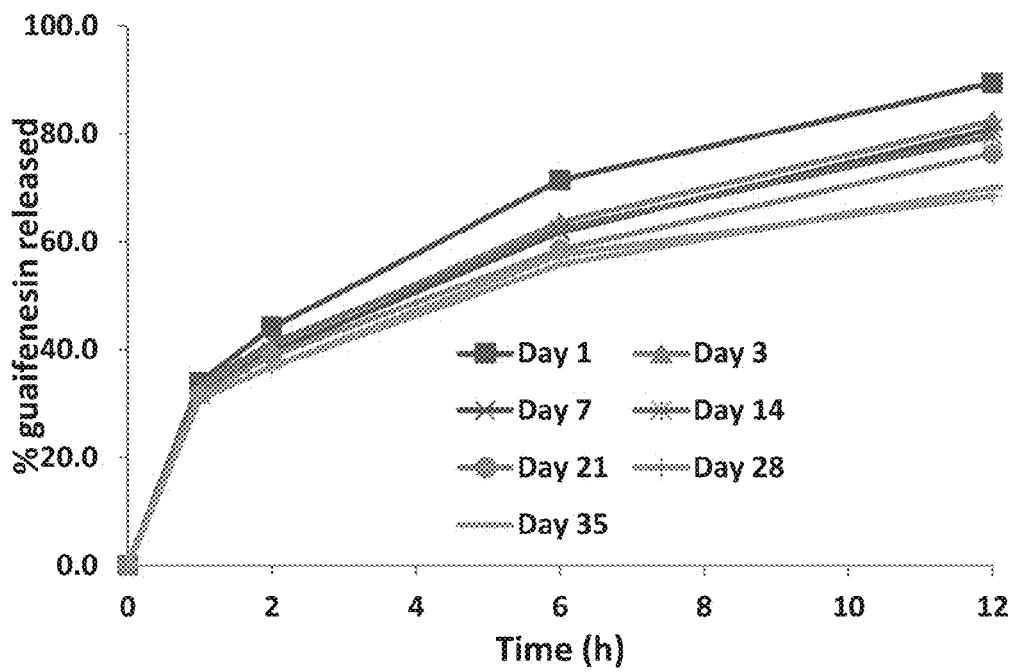
FIG. 9 is a graph showing the relationship between time and the release of guaifenesin.

An exemplary guaifenesin particle was formed with 57% carnauba wax, 10% stearic acid, 32% guaifenesin, and 1% ethyl cellulose. The release of guaifenesin from these particles was measured at 40° C. over 35 days, as described above. The results are shown in FIG. 9 and Table 3.

TABLE 3

| | Percent Release | | | | | |
|---|---|---|---|---|---|---|
| Time (h) | Day 0 | Day 7 | Day 14 | Day 21 | Day 28 | Day 35 |
| 0 | 0.0 | 0.0 | 0.0 | 0.0 | 0.0 | 0.0 |
| 1 | 33.9 | 32.3 | 31.7 | 33.6 | 31.6 | 31.0 |
| 2 | 44.1 | 40.7 | 39.6 | 41.3 | 38.9 | 36.8 |
| 6 | 71.4 | 63.6 | 61.8 | 62.3 | 58.5 | 57.6 |
| 12 | 89.4 | 82.4 | 80.9 | 79.6 | 76.3 | 68.5 |

Figure 10:
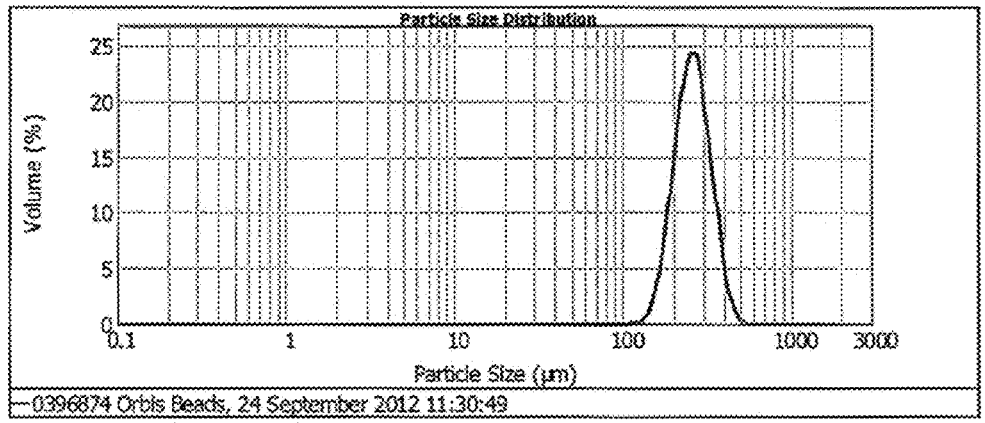
FIG. 10 is a graph showing particle size distribution results.
Figure 11:
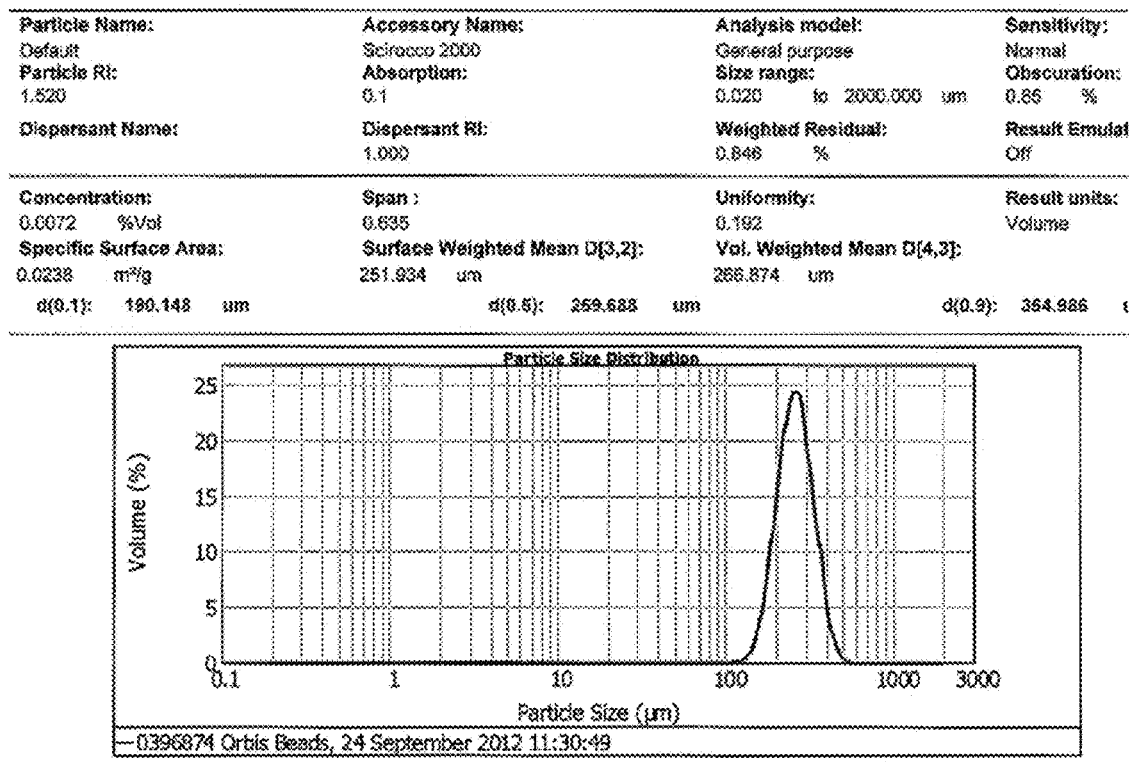
FIG. 11 is a graph showing particle size distribution results.

Particles were analyzed for their size distribution using a light-scattering apparatus (Malvern). The results are shown in FIG. 10 and FIG. 11.

Example 4

Particles Containing Ibuprofen

Ibuprofen or (±)-2-(4-isobutyl phenyl) propionic acid is a non-steroidal anti-inflammatory drug (NSAID) for the treatment of a wide range of indications, including pain, inflammation, arthritis, fever and dysmenorrhoea. In this example, particles comprising a hydrophobic matrix formed from candelilla wax and ibuprofen (Ib) as the active ingredient are prepared. Three release modifiers were studied: stearyl alcohol (SA), glyceryl monostearate (GMS), and stearic acid (ST). The particles were formed according to the schematic in FIG. 3.

Figure 4:
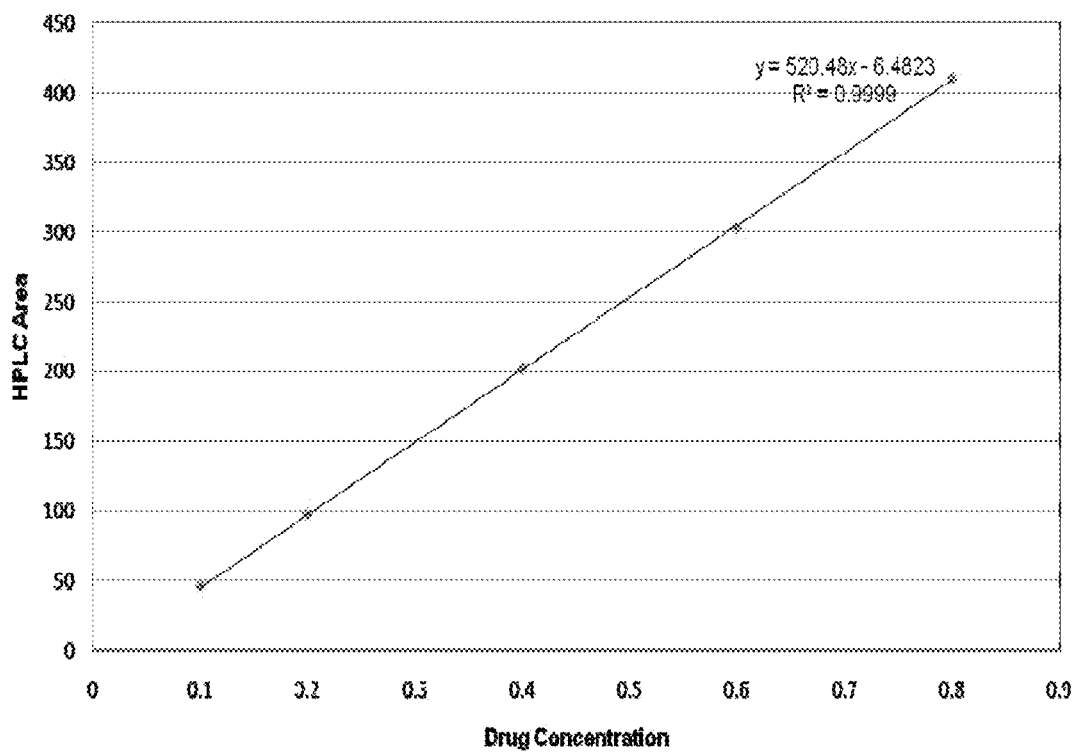
FIG. 4 is a graph depicting the relationship between active ingredient concentration and HPLC area.

The standard curve of the drug concentration of ibuprofen versus HPLC area can be seen in FIG. 4.

The amount of microspheres used for each group was selected to match the ibuprofen load of the control group (400 mg/vessel). The distance between the impeller and dissolution jar bottom was fixed at 6 cm. The impeller rotation speed was 75 rpm. The dissolution medium was 667 ml of 0.1 N HCl with 0.025 M sodium dodecyl sulphate for the first two hours. At 2 h, the dissolution medium was neutralized to pH of 6.7 by 235 ml of 0.2 M sodium phosphate tribasic and 0.025 M sodium dodecyl sulphate for the rest of study. The temperature of the medium was maintained at 37±1° C. For each sampling, 1.0 ml of dissolution media was sampled (1.0 mL) at 1, 2, 4 and 8 h. The chromatographic conditions were as follows: column: Hypersil ODS (C18), particle size 5 μm, 150 mm L×4.6mm I.D., standard, injection volume: 20 μL, flow rate: 2.0 ml/minutes, detector: UV at 254 nm, mobile phase: (500: 477:3 Acetonitlie:DI water:Glacial Acetic Acid) 0.025 M sodium dodecyl sulfate, retention time: 7 minutes. Study results are shown in FIGS. 5-7.

Figure 5:
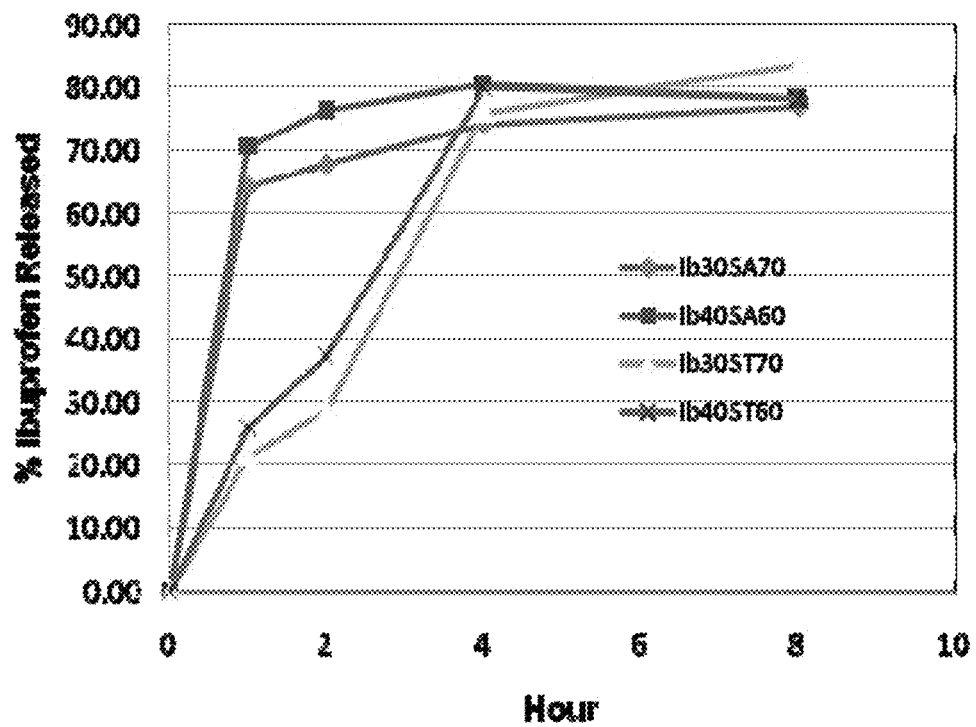
FIG. 5 is a graph showing the release profile for particles in which ibuprofen (Ib) is the active ingredient and where the particles also include different amounts of stearic acid (ST) and steryl alcohol (SA). Ib30SA70 means that 30% drug loading has been used with 70% of SA.

FIG. 5 shows the release profile for particles in which ibuprofen is the active ingredient and where the particles also include different amounts of stearic acid and steryl alcohol. The particles that include stearic acid with 30% and 40% active ingredient loading provided a sustained release formulation of 4 hours.

Figure 6:
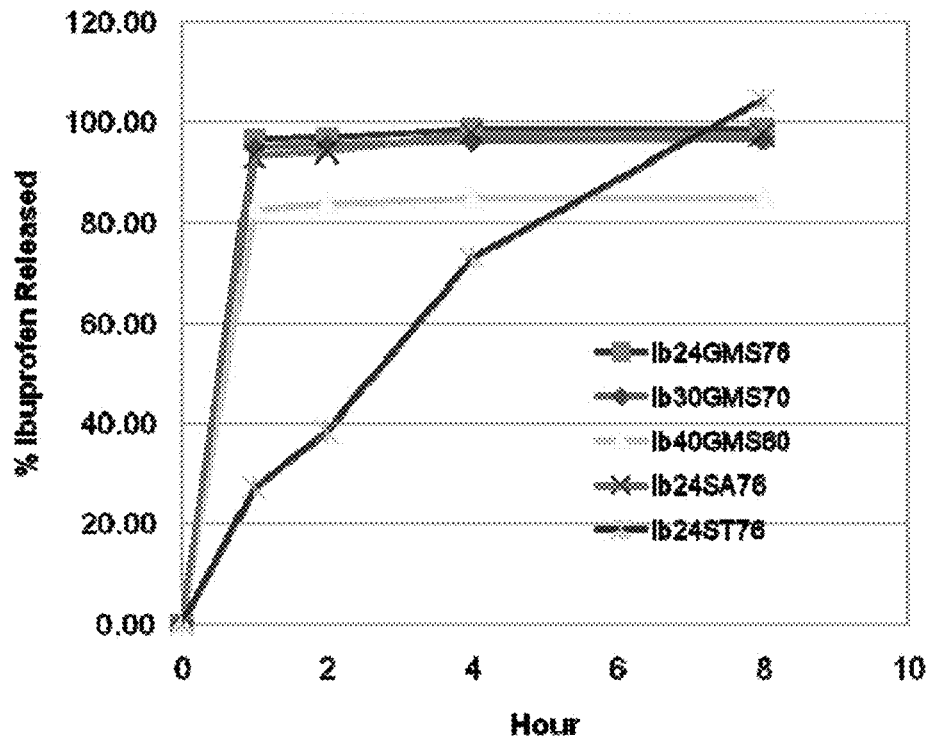
FIG. 6 is a graph showing the release profile for particles in which ibuprofen (Ib) is the active ingredient and where the particles also include different amounts of stearic acid (ST), steryl alcohol (SA), or glyceryl monostearate (GMS).

FIG. 6 shows the release profile for particles in which ibuprofen is the active ingredient and where the particles also include different amounts of stearic acid, steryl alcohol, or glyceryl monostearate. The particles that include stearic acid with 24% active ingredient loading provided a sustained release formulation of 8 hours. The particles that include gylercyl monostearate with 40% active ingredient loading provided an immediate release.

Figure 7:
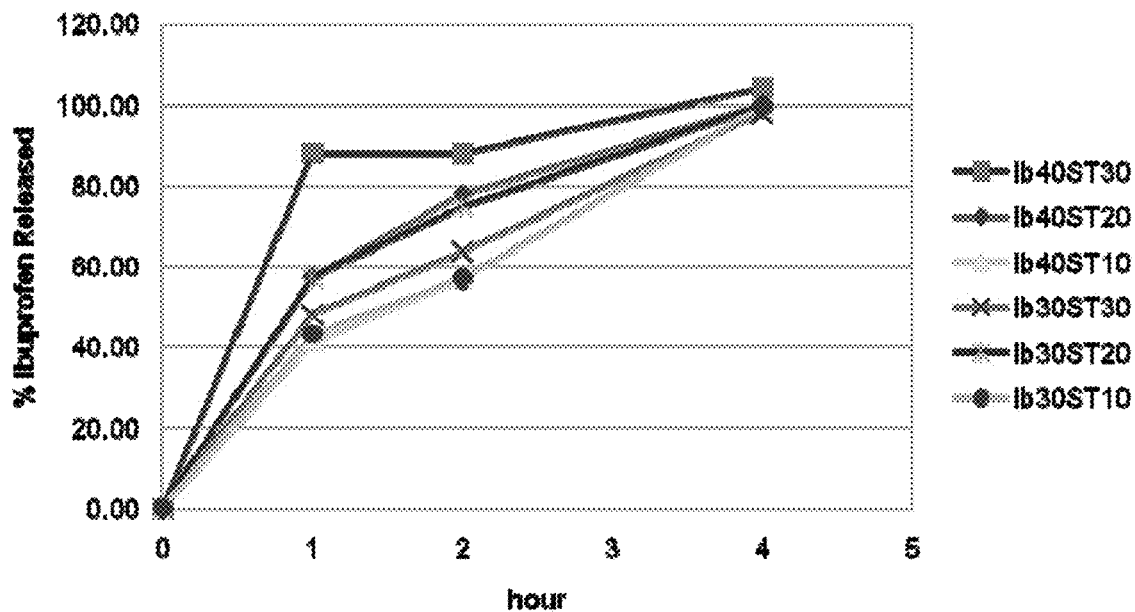
FIG. 7 is a graph showing the release profile for particles in which ibuprofen (Ib) is the active ingredient and where the particles also include different amounts of stearic acid (ST).

FIG. 7 shows the release profile for particles in which ibuprofen is the active ingredient and where the particles also include different amounts of stearic acid. The particles that provided a sustained release formulation of at least 4 hours.

Example 5

Particles Containing Guaifenesin

An exemplary guaifenesin particle was formed with 65.5% carnauba wax, 2.5% stearic acid, 32% guaifenesin. These particles did not include the optional stabilizer. Similarly, these particles were prepared as described in FIG. 3, and a comparison was made between particles that were and were not subjected to the optional post-fabrication heat treatment.

Figure 12:
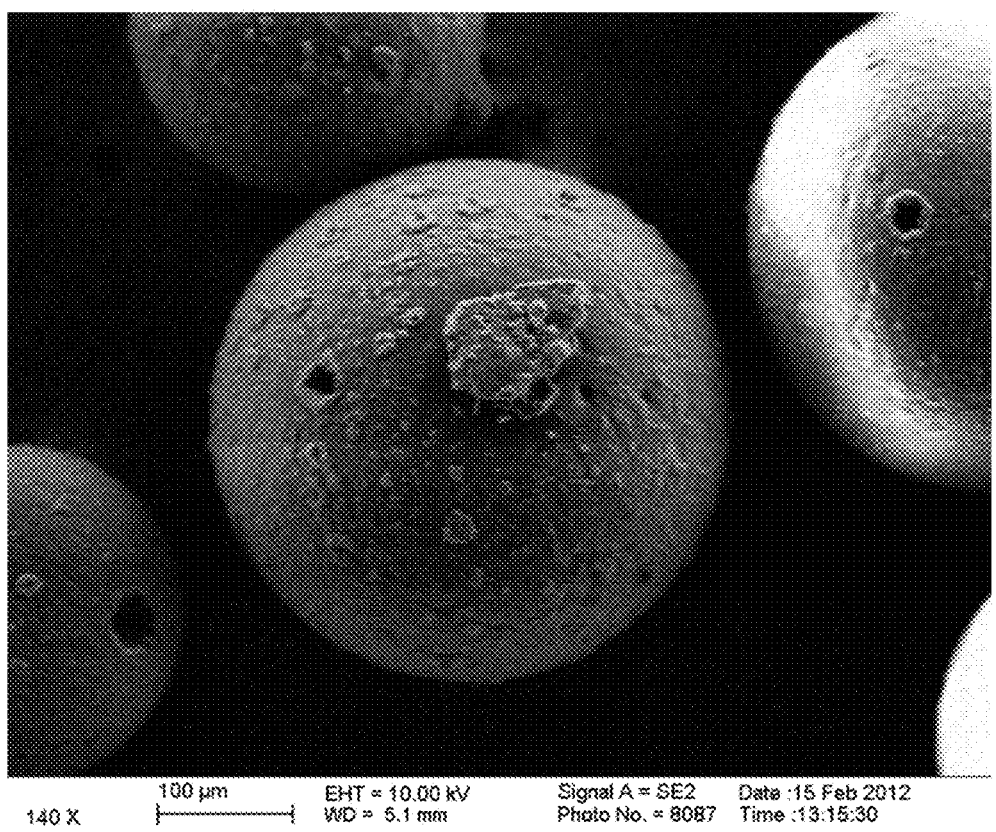
FIG. 12 is an SEM image taken at 140×.
Figure 13:
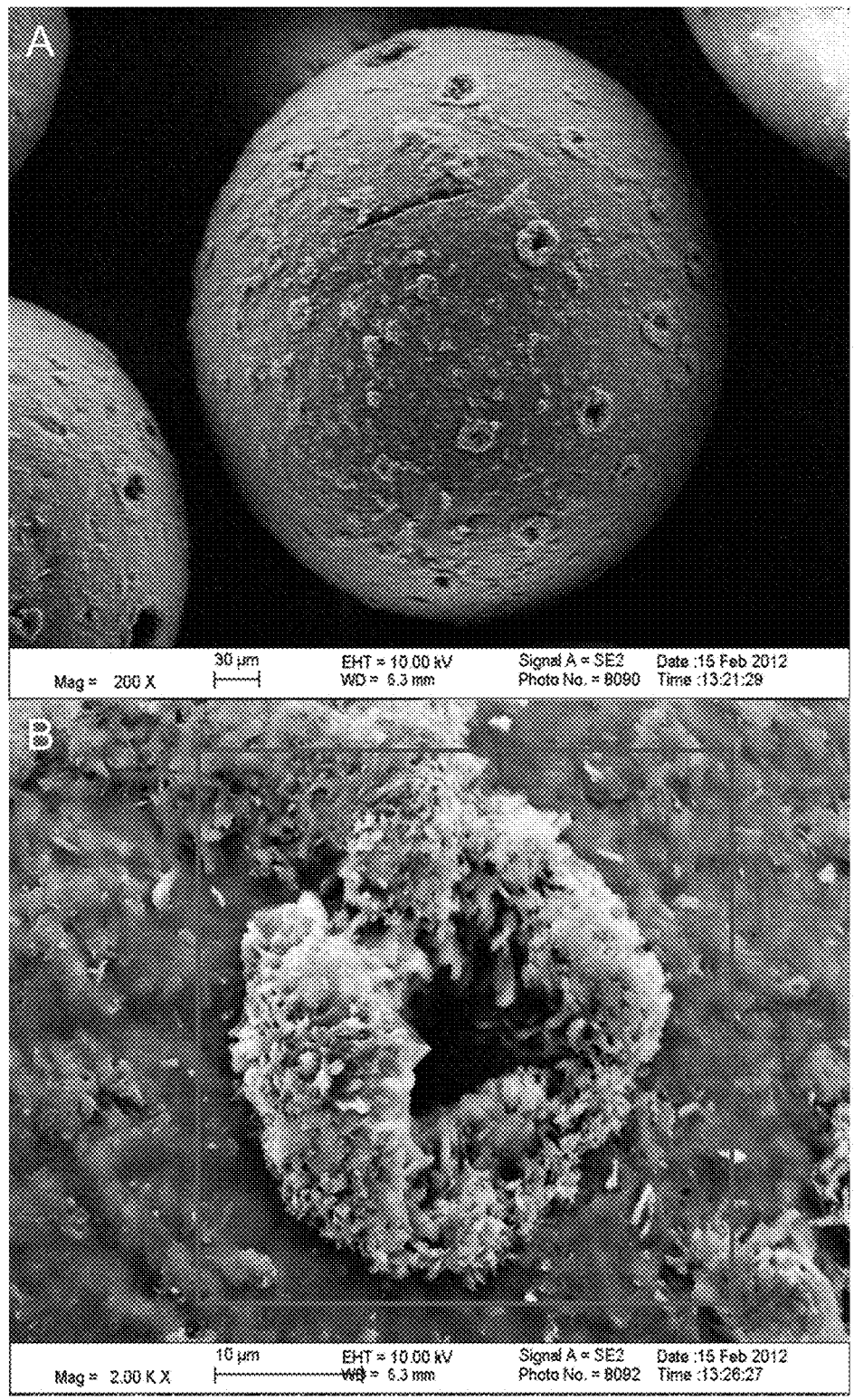
FIG. 13 is an SEM image taken at (A) 200× and (B) 2,000×.
Figure 14:
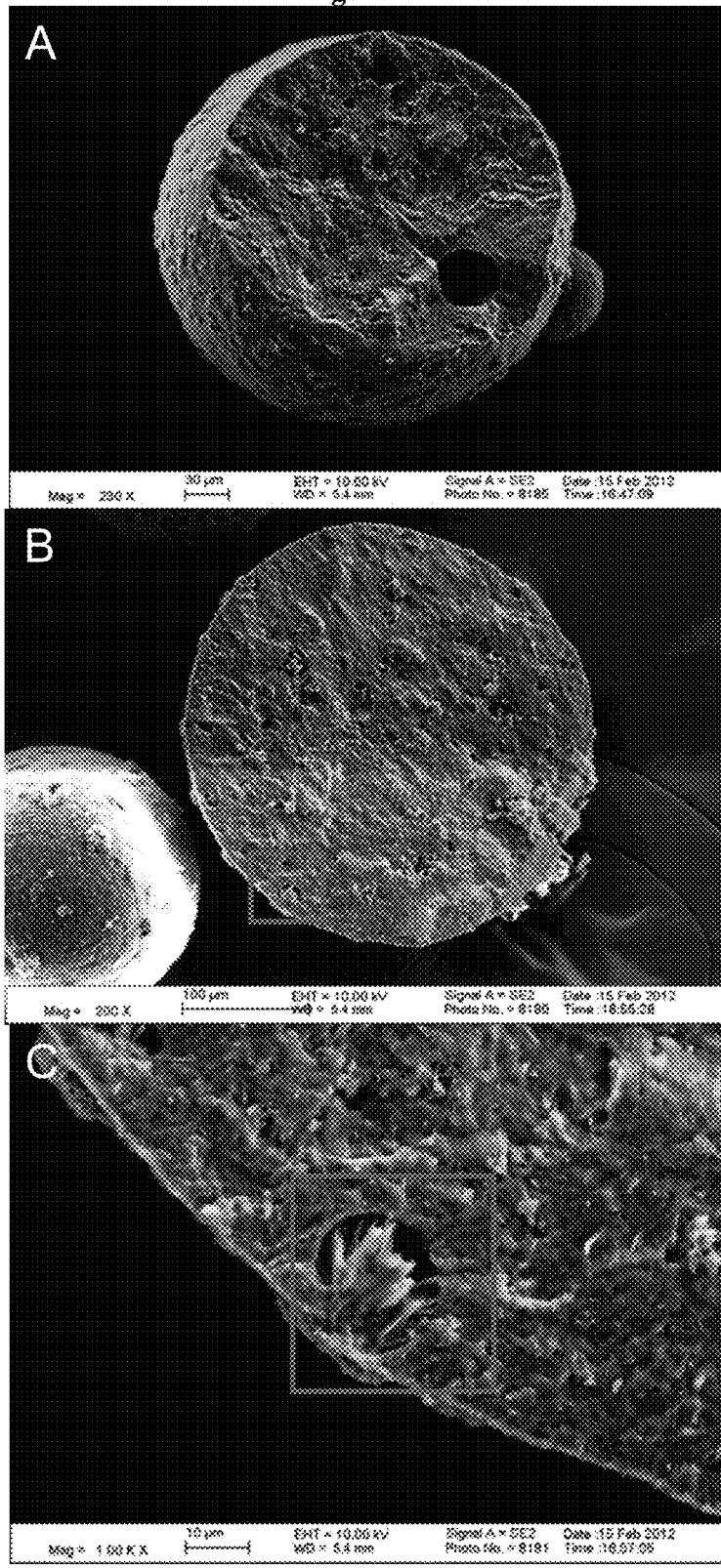
FIG. 14 is an SEM image taken at (A) 230×, (B) 200×, (C) 1,000×.

For SEM imaging, the particles were prepared by fracturing the microspheres with a razor blade. Particles were pulse sputter coated with gold. The imaging was performed using a Leo 1550 field emission scanning electron microscope at an accelerating voltage of 5 kV under a high vacuum. The spherical and uniform particle size can be seen in the SEM images in FIG. 12. Particles that were not subjected to post-fabrication heat treatment are shown in FIGS. 13A and 13B using SEM. Pores on the surface of these particles are visible. Particles that were subjected to post-fabrication heat treatment at 60° C. for 3 hours did not display surface porosity as can be seen in FIGS. 14A, 14B, and 14C. Prolonged duration of heat treatment at high temperatures can lead to excessive drug restructuring within a relaxed wax matrix under thermal expansion. This was avoided by using a stabilizer (e.g., ethyl cellulose) in particles where such restructuring was observed.

Figure 15:
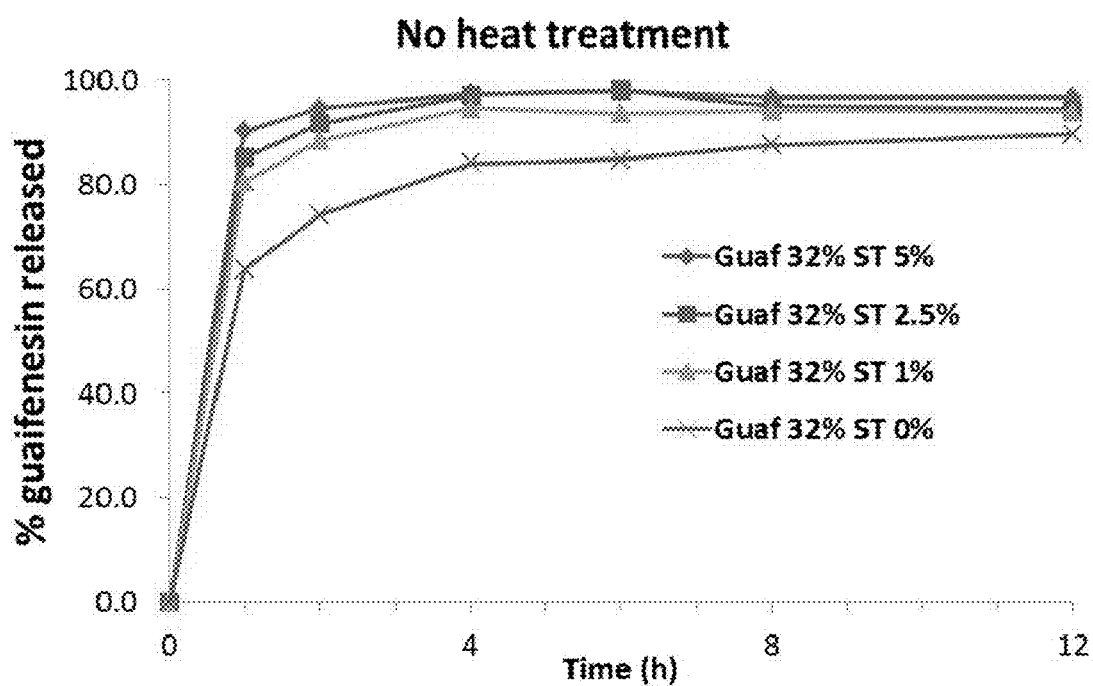
FIG. 15 is a graph showing the relationship between time and the release of guaifenesin.
Figure 16A:
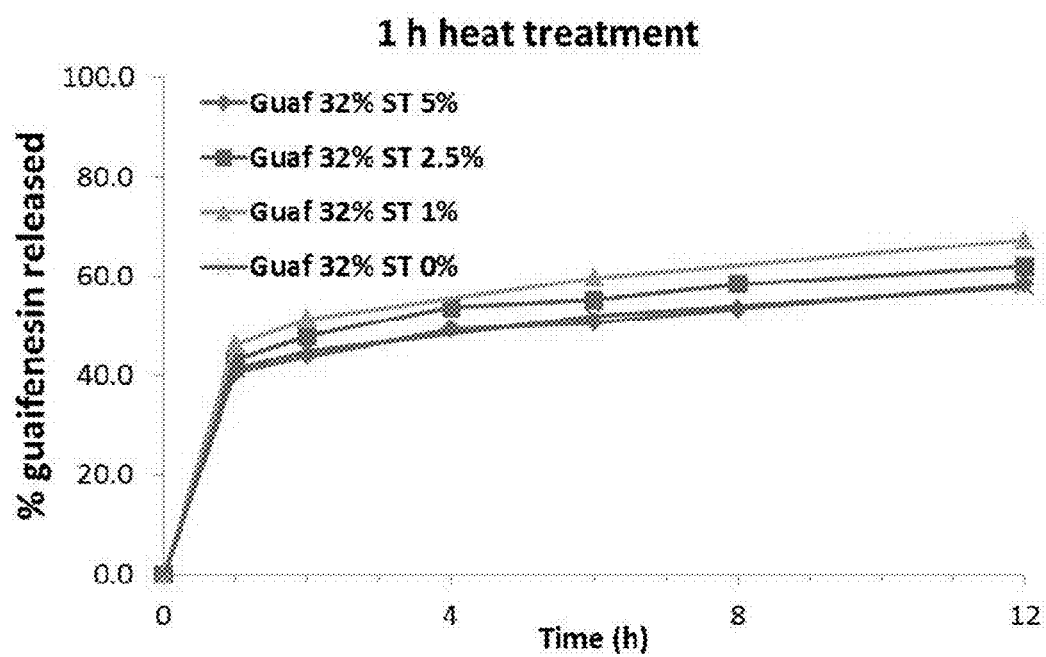
FIG. 16A is a graph showing the relationship between time and the release of guaifenesin.
Figure 16B:
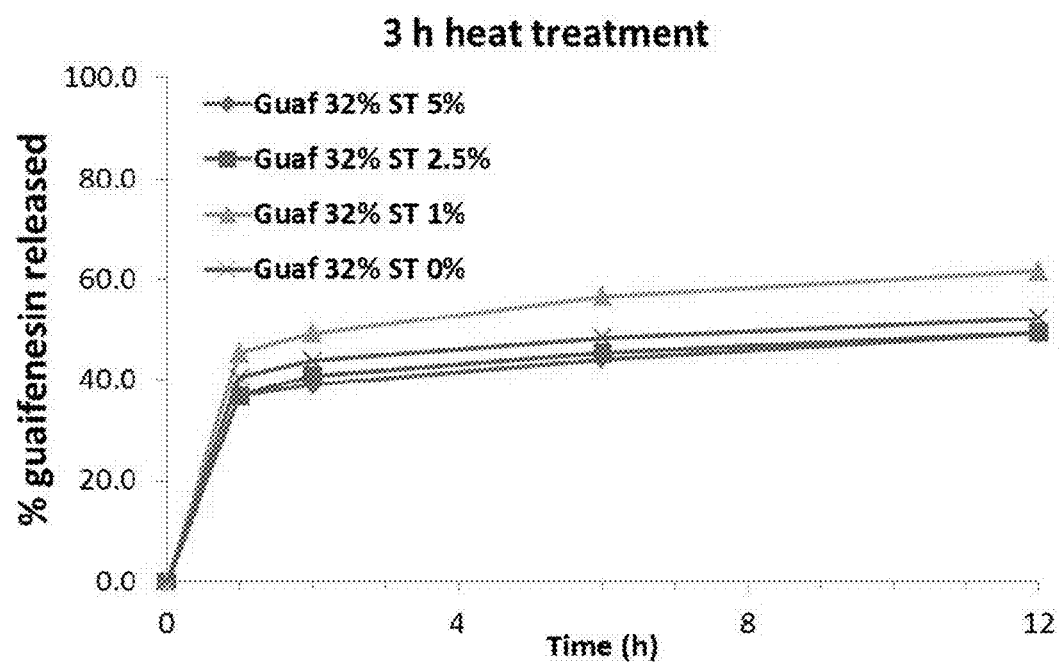
FIG. 16B is a graph showing the relationship between time and the release of guaifenesin.

A USP II dissolution study of particles with and without post-fabrication heat treatment and with different amounts of the release modifier stearic acid was performed on particles comprised of 32% guaifenesin, 0, 1, 2.5, or 5% stearic acid, and 68, 67, 65.5, or 63% camauba wax. The heat treatment reduced the percentage of active ingredient released in the first our compared to the untreated group. Compare FIG. 15 (untreated) to FIG. 16A (treated for 1 hour) and FIG. 16B (treated 3 hours).

The release modifier, stearic acid was also studied. Including stearic acid in the particles at a concentration of 1% led to a relatively higher drug release at 12 hours compared to higher (2.5% or 5%) or lower (0%) stearic acid content. Compare FIG. 15 to FIG. 16A and 16B.

Example 6

Particle Size

The particle size of various particles according to certain embodiments of the present disclosure were measured using Coulter counter (Multisizer 3) using a 560 μm aperture tube. Particles were prepared according to the methods described above. The hydrophobic matrix was either camauba wax or candellia wax, the active ingredient was ibuprofen, and stearic acid was used as the releasing agent. The components were combined using a melt-assisted dissolution of the active ingredient approach followed by particle fabrication. Particle fabrication was performed according to the system shown in FIG. 3.

Particles were formed using only the hydrophobic matrix camauba wax (i.e., no active ingredient, stabilizer, or release modifier). These particles had a mean diameter of 271 μm.

Particles formed from 67.5% candelilla wax and 30% ibuprofen and 2.5% stearic acid had a mean particle size diameter of 136 μm, and this diameter is within 25% standard deviation from the mean.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A method comprising:
   mixing a hydrophilic active ingredient, a hydrophobic matrix material, a stabilizer, and a release modifier at a temperature sufficient to melt the hydrophobic matrix thereby forming a particle mixture;
   fabricating particles from the particle mixture, wherein the particles have a particle diameter from about 50 μm to about 300 μm, and wherein the stabilizer is disposed within the hydrophobic matrix material of the particles;
   allowing the particles to cool to room temperature; and
   subsequently heating the particles to a temperature that is slightly below the melting temperature of the component of the particle having the lowest melting temperature, wherein the subsequent heating step reduces the occurrence of pores on the surface of the particle.

2. The method of claim 1, wherein the hydrophobic matrix, active ingredient, and the release modifier are mixed followed by addition of the stabilizer.

3. The method of claim 1, wherein the release modifier and the stabilizer are mixed followed by addition of the active ingredient and hydrophobic matrix.

4. A method comprising:
   melting together a hydrophilic active ingredient, a hydrophobic matrix comprising a hydrophobic wax material or a lipid material, and one or more of a release modifier and a stabilizer added to the hydrophobic matrix to form a particle mixture comprising 20 to about 60 weight % of the hydrophilic active agent, 40 to about 80 weight % of the hydrophobic wax material, about 0.5 to about 10 weight % of release modifier when present, and about 0.5 to about 10 weight % of stabilizer when present; wherein the hydrophilic active ingredient is dispersed in the hydrophobic matrix;
   fabricating particles from the particle mixture to have a mean particle diameter from about 50 μm to about 300 μm;
   allowing the particles to cool to room temperature; and
   subsequently heating the particles to a temperature that is slightly below the melting temperature of a component of the particle having the lowest melting temperature, wherein the component includes the hydrophilic active ingredient, the hydrophobic matrix, the stabilizer when present and the release modifier when present, and wherein the subsequent heating step reduces the occurrence of pores on the surface of the particle.

5. The method of claim 4, wherein the hydrophobic matrix, active ingredient, and the release modifier are melted together followed by addition of the stabilizer.

6. The method of claim 4, wherein the release modifier and the stabilizer are melted together followed by addition of the active ingredient and hydrophobic matrix.

7. The method of claim 4, wherein the active ingredient has a melting point at or below about 250° C.

8. The method of claim 4, wherein the hydrophobic matrix comprises a hydrophobic wax material.

9. The method of claim 4, further comprising allowing the particles to cool and applying an additional layer or coating to the particles.

10. The method of claim 4 wherein the release modifier and the stabilizer are melted together and the hydrophobic matrix and the active ingredient are then added.

11. The method of claim 10 wherein the release modifier is selected from the group consisting of stearic acid, sodium stearate, magnesium stearate, glyceryl monostearate, cremophor (castor oil), oleic acid, sodium oleate, lauric acid, sodium laurate, myristic acid, sodium myristate, vegetable oils, coconut oil, mono-, di-, tri-glycerides, stearyl alcohol, span 20, span 80, and polyethylene glycol (PEG).

12. The method of claim 10 wherein the release modifier is stearic acid.

13. The method of claim 10 wherein the stabilizer is selected from the group consisting of cellulose, ethyl cellulose, hydroxypropylmethyl cellulose, microcrystalline cellulose, cellulose acetate, cellulose phthalate, methyl cellulose, chitin, chitosan, pectin, polyacrylates, polymethacrylates, polyvinyl acetate, EVA resins, acetate phthalate, polyanhydrides. polyvinylalcohols, and silicone elastomers.

14. The method of claim 10 wherein the stabilizer is ethyl cellulose.

15. The method of claim 8 wherein the hydrophobic matrix comprises a wax selected from the group consisting of ceresine wax, beeswax, ozokerite, microcrystalline wax, candelilla wax, montan wax, carnauba wax, paraffin wax, cauassu wax, Japan wax, and Shellac wax.

16. The method of claim 8 wherein the hydrophobic wax material is carnauba wax.

17. The method of claim 16 wherein the release modifier is added, and wherein the release modifier is stearic acid.

18. The method of claim 17 wherein the stabilizer is added, and wherein the stabilizer is ethyl cellulose.

19. The method of claim 4 wherein the particles fabricated have a mean particle diameter of from about 50 µm to about 300 µm, and wherein the particle diameter size distribution has a standard deviation no more than 25% from the mean particle diameter.

20. The method of claim 4 wherein the particles fabricated have a mean particle diameter of from about 150 µm to about 250 µm, and wherein the particle diameter size distribution has a standard deviation no more than 25% from the mean particle diameter.

21. The method of claim 4 wherein the particles fabricated have a mean particle diameter of from about 50 µm to about 300 µm, and wherein the particle diameter size distribution has a standard deviation no more than 10% from the mean particle diameter.

22. The method of claim 4 wherein the particles fabricated have a mean particle diameter of from about 150 µm to about 250 µm, and wherein the particle diameter size distribution has a standard deviation no more than 10% from the mean particle diameter.

23. The method of claim 4, wherein the hydrophobic matrix comprises a lipid material chosen from one or more of glycerol fatty acid esters, triacylglycerols, tripalmitin, tristearin, glyceryl trilaurate, coconut oil, hydrogenated fats, ceramides, and organic esters.

24. The method of claim 4, wherein the temperature at which the particles are subsequently heated is 65° C.

25. The method of claim 4, wherein the temperature at which the particles are subsequently heated is 60° C.

26. The method of claim 4, wherein the temperature at which the particles are subsequently heated is slightly lower than the melting temperature of the hydrophobic matrix.

27. The method of claim 4, wherein the subsequent heating step is performed 6 to 24 hours after the fabrication step.

28. The method of claim 4, wherein the subsequent heating step is performed for a period of 1 hour.

29. The method of claim 4, wherein the subsequent heating step is performed for a period of 3 hours.

* * * * *